United States Patent [19]

Fabinski et al.

[11] Patent Number: 4,682,031
[45] Date of Patent: Jul. 21, 1987

[54] INFRARED GAS ANALYZER

[75] Inventors: Walter Fabinski, Kriftel; Werner Schaefer, Kronberg, both of Fed. Rep. of Germany

[73] Assignee: Hartmann & Braun AG, Frankfurt am Main, Fed. Rep. of Germany

[21] Appl. No.: 856,585

[22] Filed: Apr. 25, 1986

[30] Foreign Application Priority Data

Apr. 26, 1985 [DE] Fed. Rep. of Germany ....... 3515128

[51] Int. Cl.$^4$ ............................................. G01N 21/37
[52] U.S. Cl. ..................................... 250/345; 250/343
[58] Field of Search ...................... 250/345, 343, 344; 356/437

[56] References Cited

U.S. PATENT DOCUMENTS 4,500,207 2/1985 Maiden ................................ 250/343
4,605,313 8/1986 Kebabran ........................... 250/343

Primary Examiner—Carolyn E. Fields
Attorney, Agent, or Firm—Ralf H. Siegemund

[57] ABSTRACT

A infrared gas analyzer having measuring and reference chambers and receiving chambers respectively disposed on radiation exit sides of the measuring and reference chambers and being filled with a particular gas; a pressure communicating duct system including a particular chamber interconnects the two receiving chambers is partitioned by a foil of polyvinylidenfluoride being piezo electrically effective to generate an electrical signal on account of a pressure differential between the two receiving chambers, as indication of the concentration of the measuring gas, i.e., host gas that flows through the measuring chamber.

3 Claims, 4 Drawing Figures

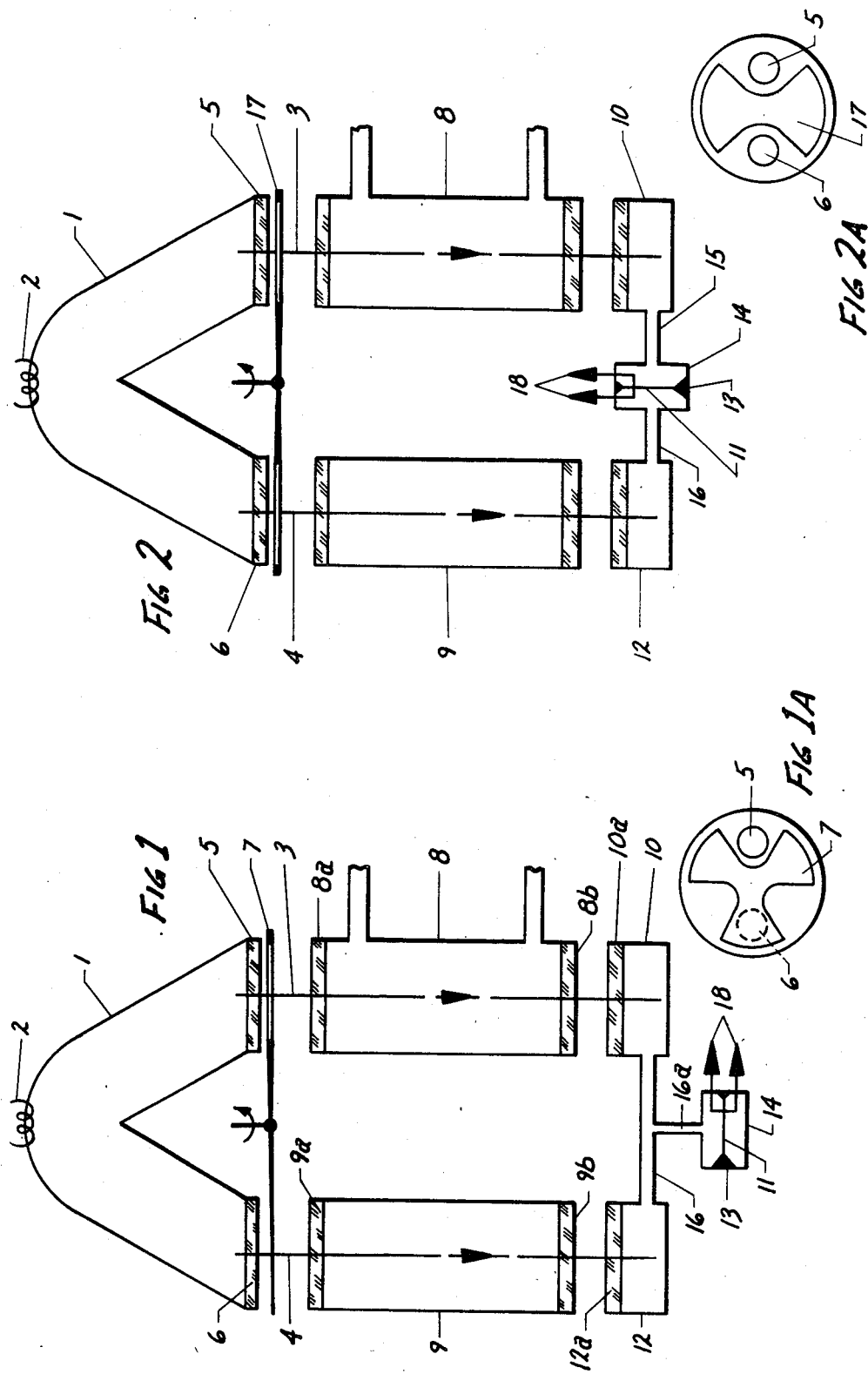

INFRARED GAS ANALYZER

BACKGROUND OF THE INVENTION

The present invention relates to an infrared gas analyzer. More particularly, the present invention relates to an infrared gas analyzer which includes a measuring chamber, container, a cuvette and a chamber, cuvette or container for a reference gas. Moreover, down stream from these two containers a radiation receiving device is provided using the principle of obtaining and ascertaining a pressure differential on account of different absorption in the receiving chambers. Infrared gas analyzers to which the invention pertains uses specific radiation absorption sections (bands) multi-atom, non-elementary gasses having particularly absorption bands in the infrared range, and the absorption cahacteristics and capabilities of such a gas are used for purposes of obtaining measurement, particularly quantitative measurements of gas components in a host gas. Upon using two parallel beams separately intercepted by receiver chambers pressure differentials are an indication of differences in absorption by the content of the measuring and reference chambers. The measuring gas is usually run through an analyzing and measuring chamber on a continuous basis. That chamber is placed in one radiation beam path. The reference chamber is disposed as stated to be passed through by the second beam and contains a gas, for example, that does not absorb infrared radiation. Depending upon the concentration of the measuring component in the host gas that flows through the analyzing and measuring chamber, and with reference to a (normally) constant value as provided through the reference chamber, one will obtain a particular differential in radiation on the exit side of these chambers, and that differential is then measured through the receiving chambers mentioned above. Moreover, the beams are periodically interrupted (modulated) so that the relevant measuring and reference quantities appear as an amplitude modulation. The difference in radiation causes different heating and therefore different pressures in the two receiving chambers which are suitably placed to inteqcept the two beams after they traverse the measuring and reference chambers. The two receiving chambers are interconnected so that a pressure differential difference can be measured. Usually, a membrane capacitor is used here with a flexible membrane that deflects depending on the pressure differential on both of its sides, and this deflection is converted into an electrical signal to be suitably ascertained.

Infrared gas analyzers of the type mentioned above are, for example, described and disclosed in a data sheet distributed by applicant's assignee under the number 20-1.12, and published May, 1983. Further, for the state of the art generally, reference is made to the following patents by applicant's assignee: U.S Pat. Nos. 4,373,137, 4,288,693, 4,281,248, 4,190,732, 4,156,812, 3,937,962, 3,925,667, and 4,496,840. These various gas analyzers use different techniques, but in many and all instances the principle of chopped reference and measuring beams, and of separately measuring these two beams under utilization of absorption techinques then called upon in a differential mode, is widely used throughout.

DESCRIPTION OF THE INVENTION

It is an object of the present invention to provide a new and improved infrared gas analyzer using measuring and reference chambers and the two infrared receiving chambers being operatively interconnected such that a pressure differential can be measured, the pressure differential resulting from differences in absorption.

In accordance with the preferred embodiment of the present invention, the object is obtained by converting the pressure difference between the receiving chambers into electrical signals generated in that a piezo electrically effective foil of polyvinylidenefluoride is disposed in relation to these two receiver chambers such that the respective pressures act on the foil, and the foil is positioned and tensioned so as to be responsive fully to any and all pressure differentials as between the two receiving chambers. The invention can be practiced with modulations of the measuring and reference beams being in phase or out of phase. The interconnecton between the receiving chambers and the membrane differs in the two cases.

DESCRIPTION OF THE DRAWINGS

While the specification concludes with claims particularly pointing out and distinctly claiming the subject matter which is regarded as the invention, it is believed that the invention, the objects and features of the invention, and further objects, features and advantages thereof will be better understood from the following description taken in connection with the accompanying drawings in which:

FIG. 1 illustrated an example of the preferred embodiment of the present invention for practicing the best mode thereof with out of phase modulation;

FIG. 1a is a schematic showing of the modulation producing diaphragm in FIG. 1;

FIG. 2 is view similar to FIG. 1 but showing in-phase operation; and

FIG. 2a is the companion showing for the diaphragm.

Proceeding now to the detailed description of the drawings, the figures illustrate generally a radiation guide path 1 which on the basis of a infrared light source 2 generates two parallel beams 3 and 4. These beams exit through the windows 5 and 6, respectively, and pass, respectively, through a measuring chamber, cuvette, retort, or the like, 8, and through reference chamber, cuvette, retort, or the like, 9. The chamber 8 is flown through by a gas which is composed of a host gas and of a measuring component or measuring gas possibly being of a spurious nature, but of variable concentration. The principal object of the device is to measure quantitatively the concentration of this measuring gas within the host gas. The chamber 8 has entrance and exit windows 8a and 8b, respectively, and infrared radiation that is permitted to pass through the exit window 8b on account of not having been absorbed inside of the chamber 8 is received by a receiving chamber 10 having an entrance window 10a.

The reference beam 4, so to speak, after leaving the window 6 runs through the reference chamber 9 having entrance windows 9a and exit window 9b. This chamber contains a gas which does not or hardly absorbs infrared radiation, such as nitrogen. The infrared radiation which is permitted to pass through the exit windows 9b of reference chamber 9 is received by a receiving chamber 12 having an entrance window 12a.

In between the set of windows 5 and 6 on one hand, and the set of windows 8a and 9a on the other hand, there is provided a rotating diaphragm wheel 7 denoted in FIGS. 1 and 1a and 17 in FIGS. 2 and 2a. The wings of the diaphragm wheel are such that they block any infrared radiation completely. This diaphragm wheel 7 alternatingly interrupts beams 3 and 4 (out of-phase operation) during the measurement, and therefore introduces an intensity modulation upon the two beams. The diaphragm 17 interrupts both beams simultaneously (in-phase operation).

The receiving chambers 10 and 12 of the detecting device operate selectively. They do contain the gas which is the same or of the same type that is to be measured within the host gas flowing through the chamber 8. If it is said that this gas in the chambers 10 and 12 is to be of the same type, this feature refers to equality or strong similarity in relevant absorption lines and bands.

As a consequence of absorption, for example, of radiation in the receiving chamber 10, the pressure in that chamber alternates with the modulation. This absorption variation has to be distinguished from absorption variations (and possible pressure changes) in the measuring chamber 8. Pressure variations also obtain in the other receiving chamber, namely, receiving chamber 12 on account of modulation. These pressure variations are out of phase in the example of FIG. 1 and in phase in the example of FIG. 2. The absorption variations in the chamber 8 in either case depends upon the concentration of the measuring component within the measuring gas that flows through the chamber 8, while the pressure variations in the chamber 10 is dependent from such variations only to the extent absorption variations in chamber 8 may be attributable to variations in concentration of the measuring gas. The reference chamber 9 does not contain the measuring gas nor is it subject to any variations thereof. As a consequence pressure differences obtain between the chambers 10 and 12 and a running indication is available on the concentration of measuring gas.

In FIG. 1 these two receiving chambers 10 and 12 are interconnected through a duct or channel 16 leading to a branching duct 16a which leads to a membrane chamber 14. The chamber 14 is partitioned through a membrane foil 11. This foil 11 is made of polyvinylidenefluoride, and is clamped by means of clamp 13 to be taut and to be subjected fully to the altenating pressure differential in the chambers 10 and 12 on one hand and the filling of the chamber 14 on the other side of foil 11. An electrical signal is extracted from opposite surfaces of the foil 11 by means of terminals 18.

In FIG. 2 the two chambers 10 and 12 are not directly interconnected. Rather, there is a a first duct or channel 15, the particular membrane chamber 14, and another duct 16, whereby particularly the two ducts 15 and 16 should have quite similar dimensions so as to provide for similar conditions inside of the membrane chamber 14. Also here the chamber 14 is partitioned through the membrane foil 11. Likewise foil 11 is made of polyvinylidenefluoride, and is clamped by means of clamp 13 to be taut and to be subjected fully therefore to the pressure differential in the chambers 10 and 12 and which is effective on the foil 11 via the ducts 15 and 16 and the two sides of the partitioning in chamber 14. An electrical signal is extracted from opposite surfaces of the foil 11 by means of terminals 18.

The foil 11, since it is made of polyvinylidenefluoride, acts piezo-electrically and is tensioned so as to be fully responsive to pressure variations as they occur in the two chambers 10 and 12. In order to prevent one sided accumulation of pressure, a very small aperture may be provided in the foil 11 so as to obtain long term pressure compensation as between the various chambers so that a cumulative error is not obtained.

The invention is not limited to the embodiments described above, but all changes and modifications thereof not constituting departures from the spirit and scope of the invention, are intended to be included.

We claim:

1. Infrared gas analyzer including a source of infrared radiation, a measuring chamber receiving and being passed through a first beam of infrared radiation from said source; a reference chamber disposed for receiving a second beam from said source; a first and second receiving chamber respecitvely disposed on radiation exit sides of said measuring and reference chambers and filled with a particular gas, the improvement comprising:
    a pressure communicating duct system including a particular chamber connected to said two receiving chambers; and
    a foil of polyvinylidenefluoride being piezo electrically effective and being disposed and tensioned across said particular chamber to partition said particular chamber such that the pressure from the two receiving chambers act on said foil, there being means for attracting an electrical signal from oposite surfaces of said foil.

2. Analyzer as in claim 1 and including means for out of-phase modulation of the first and second beams, the duct system interconnecting the receiving chambers directly and connecting then to one side of the particular chamber.

3. Analyzer as in claim 1 and including means for in-phase modulation of the first and second beams, the duct system connecting the receiving chambers to opposite sides of the partitioned particular chamber.

* * * * *